US006448256B1

(12) United States Patent
Wright et al.

(10) Patent No.: US 6,448,256 B1
(45) Date of Patent: Sep. 10, 2002

(54) ANTIBIOTIC PRODRUGS

(75) Inventors: George E. Wright, Worcester; Neal C. Brown, Northboro; Chengxin Zhi, Worcester, all of MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 09/576,474

(22) Filed: May 23, 2000

Related U.S. Application Data

(60) Provisional application No. 60/135,647, filed on May 24, 1999.
(51) Int. Cl.[7] ............... A61K 31/505; A01N 43/54; C07D 473/00; C07D 239/02
(52) U.S. Cl. ............ 514/269; 514/272; 514/274; 544/276; 544/277; 544/312; 544/321
(58) Field of Search ................. 514/269, 272, 514/274; 544/312, 321, 276, 277

(56) References Cited

U.S. PATENT DOCUMENTS

| | | | |
|---|---|---|---|
| 4,957,924 A | 9/1990 | Beauchamp | 514/262 |
| 5,516,905 A | 5/1996 | Brown et al. | 544/312 |
| 5,646,155 A | 7/1997 | Wright | 514/261 |

FOREIGN PATENT DOCUMENTS

| | | |
|---|---|---|
| WO | WO 96/06614 | 3/1996 |

OTHER PUBLICATIONS

Colla et al., "Synthesis and Antiviral Activity of . . . ", J. Med. Chem., 26:602–604, 1983.
Wright et al., "DNA polymerase III: A new . . . ," Current Opinion in Anti–infective Investigational Drugs, 1(1):45–48, 1999.
Beauchamp et al., "Amino acid ester . . . ," Antiviral Chemistry & Chemotherapy; 3(3):157–164, 1992.

*Primary Examiner*—Mukund J. Shah
*Assistant Examiner*—Tamthom N. Truong
(74) *Attorney, Agent, or Firm*—Fish & Richardson P.C.

(57) ABSTRACT

The invention relates to prodrugs of N-substituted derivatives of 6-aminouracils, 6-aminoisocytosines, guanines, and 2-aminoadenines. The N-linked substituents include an ester group that is cleaved upon administration into a subject to yield a substituent having a terminal hydroxyl group. Pharmaceutical compositions including these compounds, and methods for treating Gram-positive bacterial infections using these compounds, are also disclosed.

28 Claims, 2 Drawing Sheets

FIG. 1  TIME AFTER INJECTION (MIN)

ANTIBIOTIC PRODRUGS

CROSS-REFERENCE TO RELATED APPLICATION

This application claims the benefit of U.S. Provisional Application Serial No. 60/135,647, filed May 24, 1999, which is incorporated herein by reference in its entirety.

STATEMENT AS TO FEDERALLY SPONSORED RESEARCH

The invention described herein was supported in whole or in part by STTR grant number 1 R43 AI42160 from the National Institutes of Health. The government has certain rights in the invention.

FIELD OF THE INVENTION

The invention relates to antibiotic prodrugs and organic chemistry.

BACKGROUND OF THE INVENTION

The management of life-threatening diseases caused by multi-antibiotic-resistant (MAR) bacteria has become a major clinical and public health problem. One approach to solving this problem is the identification of new antibiotic targets and the development of target-selective "bullets."

Gram-positive bacterial DNA polymerase III, an enzyme essential for replication of the bacterial chromosome, is an attractive target. A number of N3-substituted 6-anilinouracils and 6-benzylaminouracils have been shown to inhibit the activity of this enzyme. These compounds base-pair with an unopposed template cytosine in the enzyme's DNA template and insert the anilino group into a specific "receptor" within the enzyme's dNTP-binding site. The base-pairing and receptor binding create a non-productive ternary complex of enzyme, inhibitor, and primer-template, thereby inhibiting replication of the bacterial chromosome and thus presenting bacterial reproduction, thereby inhibiting replication of the bacterial chromosome and thus preventing bacterial reproduction.

SUMMARY OF THE INVENTION

The invention is based on the discovery that certain prodrugs of ring N-substituted derivatives of 6-aminouracils, 6-aminoisocytosines, guanines, and 2-aminoadenines have advantageous properties, such as greater water solubility or greater oral bioavailability, than the ultimate drugs. The N-linked substituents generally include esters, such as amino acid esters and dicarboxylic acid esters. Upon administration into an animal, the prodrugs are converted into bioactive drugs by cleavage of the ester bond, e.g., via endogenous esterases. The prodrugs can therefore be formulated into compositions for treating Gram-positive bacterial infections.

The invention features compounds having the formulas:

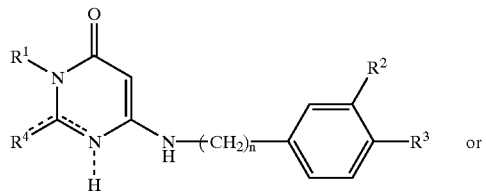 or

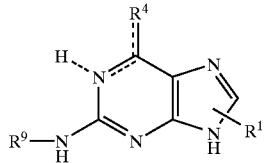

where $R^1$ is —(CH$_2$)$_a$—(CHOH)$_b$—(CH$_2$)$_c$—O—C(=O)—(CH$_2$)$_d$-CHR$^5$-R$^6$, where a is 1–4; b is 0 or 1; c is 1–5; d is 0–4; n is 0 or 1; $R^5$ is the side chain of an amino acid; $R^6$ is —COOH —COO$^-$M$^+$, or —NH$_2$; each of $R^2$ and $R^3$ is, independently, linear C$_{1-6}$ alkyl, branched C$_{3-6}$ alkyl, linear C$_{1-6}$ haloalkyl, branched C$_{3-6}$ haloalkyl, halo, or $R^2$ and $R^3$ together are a bivalent moiety having the formula —(CH$_2$)$_3$—; M$^+$ is a pharmaceutically acceptable counter-ion, such as Na$^+$; $R^9$ is a moiety containing an aryl group; and $R^4$ is =O or —NH$_2$, or a pharmaceutically acceptable salt thereof. For example, $R^2$ can be ethyl or iodo, and $R^3$ can be methyl. Upon administration of the prodrug into a subject, e.g., a mammal such as a human, $R^1$ of the compound is cleaved at the ester group to produce the drug.

The dotted lines representing chemical bonds in the structures described herein denote changes in valency when, e.g., $R^4$ is =O versus —NH$_2$ in the structures described above.

In certain embodiments, $R^5$ is the side chain of a naturally-occurring amino acid, e.g., an amino acid of animal, plant, fungal or bacterial origin. For example, when d=0, $R^5$ can be the side chain of glycine, alanine, valine, leucine, isoleucine, glutamic acid, glutamine, aspartic acid, asparagine, lysine, phenylalanine, serine, proline, or ornithine. When d=1, $R^5$ can be the side chain of beta-alanine. When d=2, $R^5$ can be the side chain of gamma-aminobutyric acid. In other embodiments, a is 1, b is 0, c is 3, d is 0 or 1–4, and n is 0. The stereochemical configuration of any chiral carbon atom, including the carbon bonded to $R^4$, can be S or R. $R^5$ can also be the side chain of synthetic non-naturally occurring amino acids.

The invention also features a pharmaceutical composition containing a compound of the invention (e.g., a racemic mixture thereof) and a pharmaceutically acceptable carrier. Also featured is a method of treating a Gram-positive bacterial infection in a subject (e.g., a mammal such as a human) by administering to the animal a therapeutically effective amount of a compound of the invention.

In another aspect, the invention includes a method of producing a compound by combining an amino acid or an amino acid anhydride with a compound having the formula

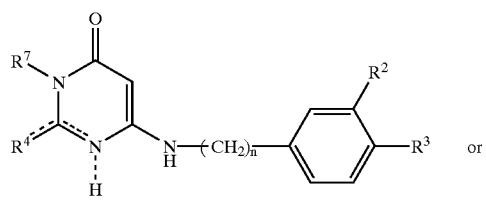 or

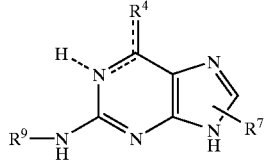

where $R^7$ is —(CH$_2$)$_a$—(CHOH)$_b$—(CH$_2$)$_c$—R$^8$, where a is 1–4; b is 0 or 1; c is 1–5; n each of $R^2$ and $R^3$ is, independently, linear $C_{1-6}$ alkyl, branched $C_{3-6}$ alkyl, linear $C_{1-6}$ haloalkyl, branched $C_{3-6}$ haloalkyl, halo, or $R^2$ and $R^3$ together are a bivalent moiety having the formula —$(CH_2)_3$—; $R^8$ is, e.g., —OH, -halo, —$OSO_2CH_3$, —$OSO_2CF_3$, or $OSO_2$(p-tolyl); $R^9$ is a moiety containing an aryl group; and $R^4$ is =O or —$NH_2$.

The term halo includes any of F, Cl, Br and I. The term haloalkyl includes any of mono-, poly- and per-haloalkyl groups.

A pharmaceutically acceptable counter-ion is any positive or negative ion that is suitable in pharmaceutical formulations, including, without limitation, sodium, potassium, ammonium, phosphate, and chloride ions.

A therapeutically effective amount is an amount sufficient to decrease by 90% or less (e.g., 90, 95, 99, 99.9, or 99.99% or less) the number of bacteria in a subject, e.g., a mammal, as determined by standard assays and compared to a control number (e.g., the number of bacteria in a placebo-infected control subject). For example, a volume of a body fluid (e.g., blood, serum, cerebral spinal fluid, seminal fluid, or urine) can be obtained from the animal after administration of a compound of the invention. The number of bacteria can then be determined by diluting the fluid, plating on appropriate solid media, and comparing to a control number of bacteria (e.g., the number of bacteria in a fluid of a placebo-treated subject). If a therapeutically effective amount of the compound was administered, the number of bacteria after administration should be less than the control number. Alternatively, a solid or semi-solid tissue of a body (e.g., fecal matter) can be suspended in a fluid, and the fluid assayed for bacteria as described immediately above.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Prodrugs have many useful properties. For example, a prodrug may be more water soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue. The use of prodrugs therefore enables the rapid development of effective, easily-administered antibiotic formulations for use in human patients suspected of having a bacterial infection or human patients in which prevention or amelioration of a subsequent bacterial infection is desired.

Other features and advantages of the invention will be apparent from the following detailed description, and from the claims.

DETAILED DESCRIPTION

Figure 1:
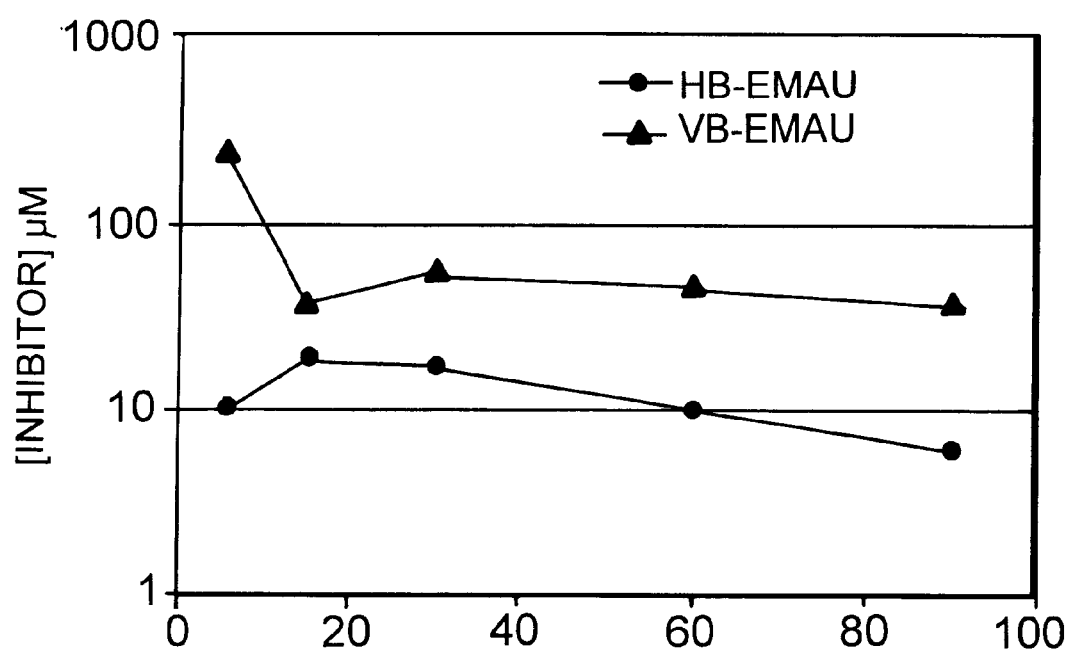
FIG. 1 is a line graph of time after injection versus prodrug concentration.

The invention relates to prodrugs of N-substituted derivatives of aminouracils, aminoisocytosines, guanines, and aminoadenines. The N-linked substituents include an ester group that is cleaved upon administration into a subject to yield a substituent having a terminal hydroxyl group. The prodrugs have the general formula of

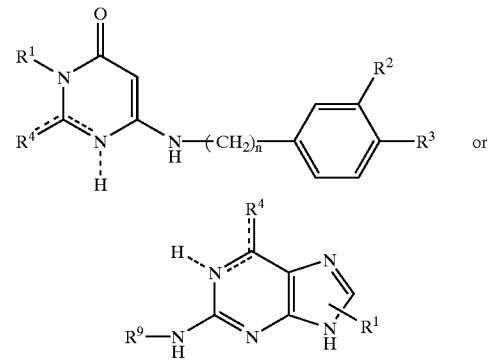

in which $R^1$ contains an ester linkage; each of $R^2$ and $R^3$ is, independently, an alkyl, halo, or haloalkyl group; $R^4$ is =O or —$NH_2$; and n is 0 or 1.

Upon administration into a subject, these prodrugs produce two general classes of drugs. The first class of drugs is of the general formula

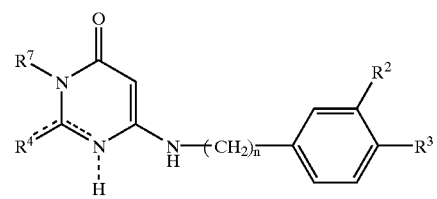

where $R^7$ is —$(CH_2)_a$—$(CHOH)_b$—$(CH_2)_c$—OH, where a is 1–4; b is 0 or 1; c is 1–5; n is 0 or 1; each of $R^2$ and $R^3$ is, independently, linear $C_{1-6}$ alkyl, branched $C_{3-6}$ alkyl, linear $C_{1-6}$ haloalkyl, branched $C_{3-6}$ haloalkyl, halo, or $R^2$ and $R^3$ together are a bivalent moiety having the formula —$(CH_2)_3$—; and $R^4$ is =O or —$NH_2$. When R4 is =O, the drug is a 6-aminouracil. When $R^4$ is —$NH_2$, the drug is a 6-aminoisocytosine.

The second class of drugs is of the general formula

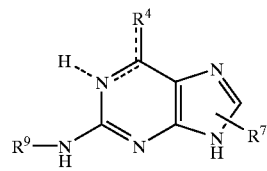

where $R^7$ is —$(CH_2)_a$—$(CHOH)_b$—$(CH_2)_c$—OH, where a is 1–4; b is 0 or 1; $R^9$ is a moiety containing an aryl group; and $R^4$ is =O or —$NH_2$. When $R^4$ is =O, the drug is a N2-substituted guanine. When $R^4$ is —$NH_2$, the drug is a 2-aminoadenine.

The 6-aminouracil type of drugs can be further divided into three subclasses of drugs:

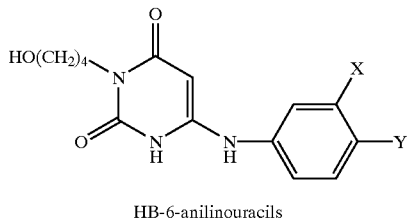

HB-6-anilinouracils

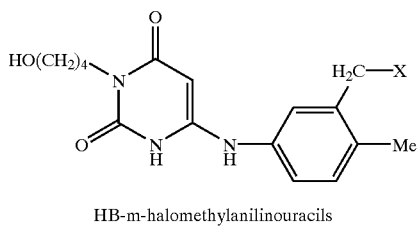

HB-m-halomethylanilinouracils

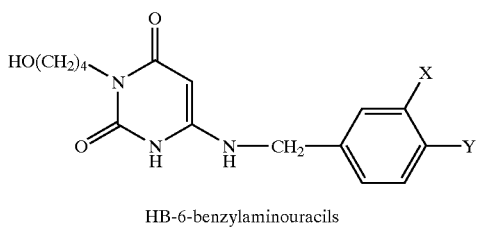

HB-6-benzylaminouracils

In these subclasses, X and Y are, independently, alkyl, halo, or haloalkyl; and HB is 4-hydroxybutyl. For the 6-anilinouracils, compounds with EMAU (6-(3-ethyl-4-methylanilino)uracil) cores are useful antibiotics.

Both 3-(2-hydroxyethyl) and 3-(3-hydroxypropyl) derivatives of EMAU (HE-EMAU and HP-EMAU, respectively) have antibacterial activity, as discussed in Example 5. However, both HE-EMAU and HP-EMAU are sometimes unstable. The presence of the reactive hydroxyl group β or γ to the pyrimidine ring causes ready cyclization under acidic or basic conditions to give furano and pyrano-pyrimidines, respectively. The biological activities of the furano and pyrano-pyrimidines is generally substantially lower than those of HE-EMAU and HP-EMAU.

The 3-(4-methoxybutyl) and 3-(4-hydroxybutyl) derivatives of EMAU, MB-EMAU and HB-EMAU, are less prone to cyclization because the hydroxyl group is not α or γ to the pyrimidine ring. These compounds are also effective antibacterial agents, as discussed in Example 6. The compound 3-(5-hydroxypentyl)-EMAU is also expected to be a useful antibacterial agent.

In addition, 6-anilinouracil compounds with IMAU (6-(3-iodo-4-methylanilino)uracil) cores are effective antibacterial agents, as discussed in Example 7.

Halomethylanilinouracils and 6-benzylaminouracils are also expected to be useful antibacterial agents because they possess potent inhibitory activity against DNA polymerase III of Gram-positive bacteria.

The new prodrugs of these compounds enhance the bioavailability and water-solubility of the above-described compounds. The prodrugs are generally more water soluble than the ultimate drugs. Water solubility is useful for making formulations suitable for intravenous administration. The prodrugs also generally have greater oral bioavailability than the ultimate drugs based on their higher solubility and increased absorption from the gastrointestinal tract. Therefore, higher and more prolonged plasma levels of the ultimate drug can be achieved when the prodrug is administered, relative to when the ultimate drug is administered. At the same time, the prodrugs have the same safety profiles as the ultimate drugs. The prodrugs are expected to be rapidly converted to the corresponding ultimate drugs by esterases circulating in the plasma.

Amino Acid Ester Prodrugs

One group of useful prodrugs includes amino acid esters. Naturally-occurring or non-naturally occurring amino acids can be used to prepare the prodrugs of the invention. For example, L-amino acids, D-amino acids, or mixtures of the L- and D-amino acids can be used. In addition, alpha-, beta-, or gamma-amino acids can be used to prepare prodrugs. Further, the substantially diverse array of naturally-occurring, non-standard amino acids found in plants can be utilized in the compounds and methods of the invention. See, e.g., Robinson, "Chapter 10: Amino Acids," In: *The Organic Constituents of Higher Plants*, pp 225–247, Cordus Press, North Amherst, Mass., 1983; and references cited therein. In particular, see pages 227–229 and 231–235. Non-standard amino acids include cysteic acid, methionine sulfoxide, methionine sulfone, gamma-aminobutyric acid, beta-alanine, alpha-methylene-gamma aminobutyric acid, beta amino isobutyric acid, gamma-amino-alpha-hydroxy-butyric acid, hypoglycine A, azetidine-2-carboxylic acid, pipecolic acid, 4-methyl proline, baikiain, beta-pyrazol-1-ylalanine, stizolobic acid, lathyrine, gamma-methylene glutamic acid, gamma-methylene glutamine, gamma-methyl glutamic acid, gamma-glutamyl ethylamide, alpha-amino adipic acid, alpha-amino pimelic acid, S-methylcysteine, methyl methionine sulfonium hydroxide, Djenkolic acid, Alliin, S-2-carboxyethyl-L-cysteine, cycloalliin, homoserine, gamma-hydroxy valine, gamma-hydroxy glutamic acid, beta-gamma-dihydroxy glutamic acid, gamma-methyl-gamma hydroxy glutamic acid, 5-hydroxy pipecolic acid, and canavanine. Non-naturally occurring amino acids useful in the compounds, compositions, and methods of this invention include cyclohexylmethyl glycine, phenyl glycine, meta-tyrosine, para-amino phenylalanine, and others known to those of ordinary skill in the art.

As shown below, the prodrug is metabolized in vivo, e.g., by esterases commonly found in the body, to yield the ultimate drug and an amino acid. In some embodiments, prodrugs are made using naturally-occurring amino acids, because the presence of natural amino acids in the body has few, if any, harmful side effects. For example, when L-amino acids are used to make prodrugs, the stereochemistry of the carbon bonded to R5 is S.

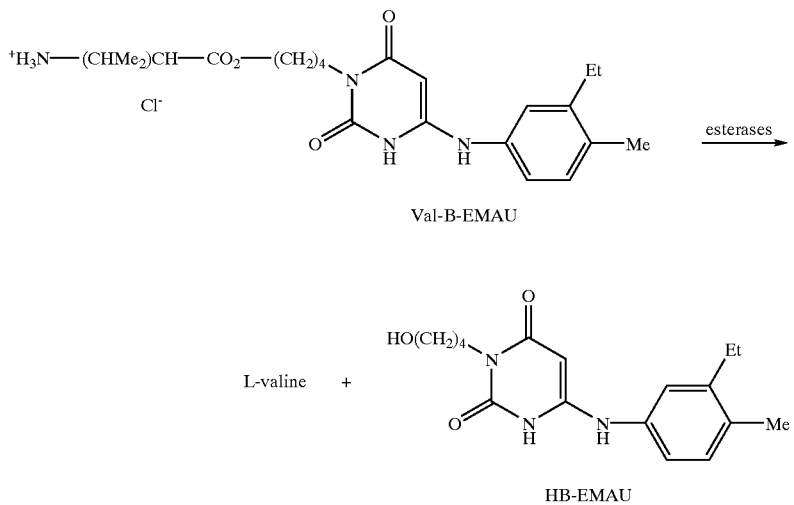

The glycyl, L-alanyl, L-valyl, L-isoleucyl, L-phenylalanyl, L-seryl, and L-prolyl esters of HB-EMAU are prepared according to the methods described in Colla, L., DeClercq, E., Busson, R. and H. Vanderhaeghe (1983) J. Med. Chem., 26:602–604; and Beauchamp, L. M., Orr, G. F., de Miranda, P., Burnette, T. and T. A. Krenitsky (1992) Antivir. Chem. Chemother., 3:157–163. Briefly, the parent compound, or a halogenated derivative of the parent compound, is condensed with an amino acid or an amino acid anhydride in an organic solvent, as shown below. The amino acid or acid anhydride can be protected with a standard amino acid protecting group. The parent drug and the amino acid are combined in a ratio of about 1:1.1 to about 1:3, for example, about 1:1.5. A catalyst, such as dimethylaminopyridine (DMAP), may be added in a stoichiometric amount. The condensation can take place at a temperature of about 20–100° C., for example, about 20–40° C. The reaction is generally complete in 3 hours to 48 hours. The amino acid is then deprotected under acidic conditions (e.g., using 0.5 N aqueous HCl) at room temperature. Two preparations are summarized below.

In the first preparatory method,

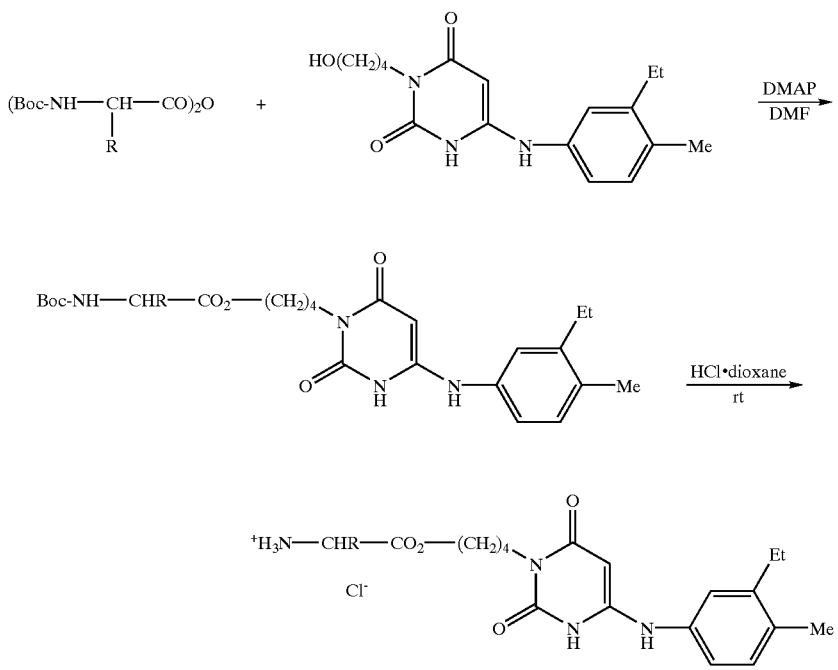

N-t-butoxycarbonyl (Boc)-protected amino acid anhydrides are condensed with HB-EMAU in the presence of dimethylaminopyridine (DMAP). The intermediates are deprotected by hydrochloric acid. The products are isolated as hydrochloride salts.

In the second preparatory method, a haloalkyl derivative instead of a hydroxyalklyl derivative is used, as shown below.

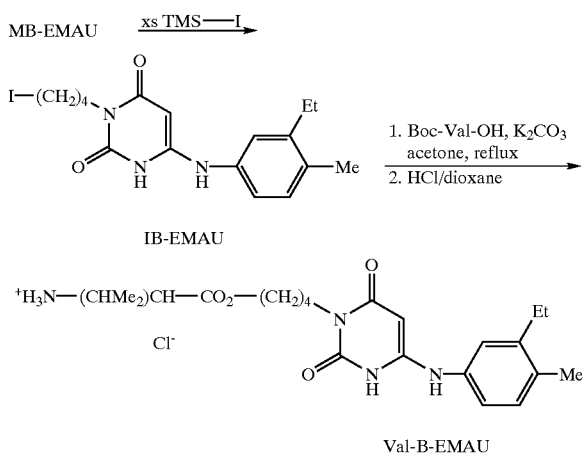

Prodrugs formed with other amino acids can be prepared using similar methods.

The amino acids used to prepare the prodrugs are selected to provide a range of oral absorption properties and hydrolysis rates. The prodrugs are generally isolated as salts. They can be isolated, for example, as the hydrochlorides, hydrobromides, sulfates, phosphates, maleates, or fumarates.

Dicarboxylic Acid Prodrugs

A second group of useful prodrugs includes dicarboxylic acid monoesters and salts thereof. These prodrugs can be prepared using bifunctional acids, as generally demonstrated in the examples that follow. The compounds can form water soluble salts that are convertible in plasma by esterases to the ultimate drug entity and an innocuous by-product (e.g., a dicarboxylic acid that is a normal body constituent).

The parent compound is condensed with a dicarboxylic acid or a dicarboxylic acid anhydride in an organic solvent, as shown below. The parent drug and the dicarboxylic acid are combined in a ratio of about 1:1.5 to 1:4, for example, about 1:2. An excess of a basic catalyst, such as triethylamine, is added. The condensation can take place at a temperature of about 20–100° C., for example, about 30–70° C. The reaction is generally complete in 6 to 24 hours. The product is treated with a basic solution, for example, a 1.25% NaHCO₃ solution, and washed on an ion exchange column to yield the final product.

As an example, HB-EMAU is treated with succinic anhydride, in the presence of a triethylamine catalyst, to give the hemisuccinyl ester in the reaction below.

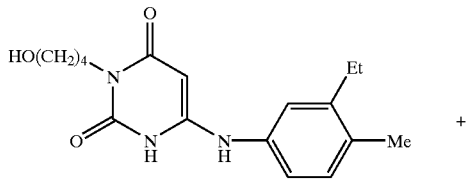

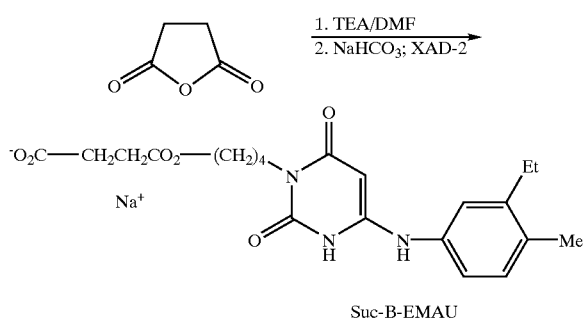

Suc-B-EMAU

Treatment with aqueous sodium bicarbonate and washing on an ion exchange column yields the sodium salt (Colla, L., DeClercq, E., Busson, R. and H. Vanderhaeghe (1983) J. Med. Chem. 26, 602–604). The monoester is cleaved to yield the ultimate drug and succinic acid, a natural product, after administration into an animal.

The dicarboxylic acid monoester prodrugs can also be prepared using other naturally-occurring diacids, such as citric acid and malonic acid. The prodrugs can be isolated as the salts, for example, as sodium, potassium, or ammonium salts. Prodrugs of the aminoisocytosine, guanine and 2-aminoadenine derivatives can be synthesized analogously.

Therapeutic Administration of Compounds

The compounds described herein are useful for the treatment of Gram-positive bacterial infections (e.g., MAR infections) in animals. The compounds of the invention can be formulated for pharmaceutical or veterinary use, optionally together with a pharmaceutically acceptable diluent, carrier, or excipient and/or in unit dosage form. In using the compounds of the invention, conventional pharmaceutical or veterinary practice can be employed to provide suitable formulations or compositions.

The formulations of this invention can be administered by any suitable route, including intravenous, subcutaneous, intramuscular, intraorbital, ophthalmic, intraventricular, intracranial, intracapsular, intraspinal, intracistemal, intraperitoneal, topical, intranasal, oral, buccal, rectal, vaginal, and bronchiopulmonary routes. The formulation can be delivered as an aerosol, dry powder, aqueous spray, or inoculum, or by scarification.

Parenteral formulations may be in the form of liquid solutions or suspensions. For oral administration, formulations may be in the form of tablets or capsules, and for intranasal formulations, in the form of powders, nasal drops, or aerosols.

Methods well known in the art for making formulations can be found in, for example, "Remington's Pharmaceutical Sciences." Formulations for parenteral administration can, for example, contain as excipients sterile water or saline, polyalkylene glycols such as polyethylene glycol, oils of vegetable origin, or hydrogenated naphthalenes, biocompatible, biodegradable lactide polymer. Carriers such as polyoxyethylene-polyoxypropylene copolymers may be used to control the release of the compounds of the invention using standard techniques. Other potentially useful parenteral delivery systems for the compounds include ethylene-vinyl acetate copolymer particles, osmotic pumps, implantable infusion systems, and liposomes. Formulations for inhalation may contain excipients, for example, lactose, or can be aqueous solutions containing, for example, polyoxyethylene-9-lauryl ether, glycocholate, and deoxycholate, or may be oily solutions for administration in the form of nasal drops, or as a gel to be applied intranasally.

Formulations for parenteral administration may also include glycocholate for buccal administration, methoxysalicylate for rectal administration, or citric acid for vaginal administration.

The concentration of the compound in the formulations of the invention will vary depending upon a number of factors, including the dosage to be administered, and the route of administration.

In general terms, the compounds of the invention can be provided in an aqueous physiological buffer solution containing about 0.1 to 10% w/v compound. General dose ranges are from about 0.01 mg/kg to about 1 g/kg of body weight per day, for example, a dose range from about 0.1 mg/kg to 100 mg/kg of body weight per day. The dosage to be administered is likely to depend upon the type and extent of progression of the infection being addressed, the overall health of the patient, and the route of administration. For topical and oral administration, formulations and dosages can be similar to those used for other antibiotic drugs, e.g., erythromycin.

Prodrug Conversion Measurements

The conversion rate of prodrugs can be measured by first establishing a reverse phase HPLC method for the detection of both prodrug and drug in a biological sample such as plasma or serum. A stock solution of prodrug, usually in saline, is diluted 1:5 in animal plasma or saline. The plasma does not need to be fresh, and plasma that is collected, frozen on dry ice, and stored at $-20°$ C. is suitable. If necessary, the sample can be thawed in a $37°$ C. water bath. Aliquots of the diluted sample are taken at 15, 30, 45, 60, 90, 120, and 180 minutes. Longer time points are usually needed for saline solutions because the rates of spontaneous hydrolysis are much longer than for enzyme-catalyzed hydrolysis. The aliquots are analyzed at a 1:10 dilution using HPLC, and the fraction of prodrug which has been converted at each time point calculated. This data can be used to approximate a half-life for the conversion of prodrug in plasma, saline, or any other biological fluid.

Selection of Candidate Prodrugs and Strategy for In Vivo Analysis in Mice The substituents attached to enhance aqueous solubility and bioavailability in vivo might not be hydrolyzed under conditions of in vitro analysis, particularly under conditions of a pol III or bacterial growth inhibition assay. Accordingly, it is possible that these potential "prodrug" forms may display in vitro behavior different from that of the "core" molecule from which they were constructed. Therefore, to avoid eliminating prodrugs with the potential for enhanced uptake and release of active forms in vivo, these compounds are subjected, regardless of their in vitro behavior, to the "screening" step of in vivo analysis described below.

Step 1: Screening—Each candidate prodrug is screened for activity in an ip/ip S. aureus protection model. Candidates that display efficacy equivalent to that of HB-EMAU and HB-IMAU are selected for advanced pharmacokinetic analysis and application in the more relevant mouse thigh model of infection.

Step 2: Rescreen "inactive" prodrug forms—Many prodrugs, particularly those which are marginally active on the isolated enzyme and on bacterial growth, might not show acceptable activity in the ip/ip screen because they are not cleaved adequately via this specific parenteral route of administration. These compounds are rescreened in a "ip/po" model in which the drug is administered orally. The compounds are given by oral gavage at a single dose of 100 mg/kg. Any compound which yields protection in 50% of animals at this dose are retained as candidates for advanced pharmacokinetic analysis and application in the thigh model of infection, as described below.

Pharmacokinetic Analysis

To qualify for application in the thigh infection model, each new prodrug candidate is generally evaluated with respect to pharmacokinetics. The steps in this evaluation are generally as follows:

(a) development of analytical methods to quantitate agents in plasma;

(b) design of optimal formulation(s) for parenteral and oral administration;

(c) determination of "immediate" dose-dependent toxicity;

(d) determination of half-life and volume of distribution (Vd) following intravenous (iv) injection; and (e) determination of uptake from subcutaneous (sc), intraperitoneal (ip), and oral (po) routes.

(a) Development of analytical methods. An HPLC-based method which can detect both the precursor and the product in a single run is developed. If a single system cannot be found, a suitable HPLC-based method is developed to quantitate each of the two drug forms separately.

(b) Design of formulation(s) for parenteral and oral administration. The choice of vehicles for administration is dictated primarily by the physicochemical properties of each agent and the intended route of its administration. The prodrugs are expected to have aqueous solubilities sufficient to permit their dissolution and administration in saline by any route.

(c) Determination of the limits of "immediate" toxicity of iv-administered drug. Each agent is dissolved in saline and administered via the tail vein, e.g., in a volume of 0.05–0.2 ml at doses of 25, 50, 100 and 150 mg/kg (two animals per dose plus two animals as vehicle controls). The animals are observed closely, e.g., for 12 hours for signs of acute toxicity. Doses which cause more than temporary discomfort are noted, and as dictated by the severity of signs of toxicity (e.g., lethargy, shivering, tendency to immobility, and "hunchbacking"). These animals are humanely euthanized by decapitation after confinement in rodent restrainers ("DecapiCones"). All animals are euthanized by the same method at the end of the observation period (e.g., 24 hours).

(d) Elimination halfife and apparent volume of distribution. An appropriate dose of each agent (the maximum permitted by the results of the above dose/toxicity studies) is injected via the tail vein to a series of mice (e.g., 12). At specific times following injection (e.g., 10, 20, 30, 45, 90, and 150 minutes), mice (e.g., a pair) are restrained in DecapiCones and decapitated, and their blood collected individually by exsanguination into a sterile test tube.

The blood samples are centrifuged to yield clear plasma (yield: 0.4–0.6 ml per mouse). Approximately 0.2 ml of the plasma sample are used for HPLC analysis, using conditions established herein for quantitation of the compound. The individual plasma levels for each time point are averaged, and the data are analyzed to estimate Vd and half-life by established methods (Gibaldi, M. and D. Perrier. Pharmacokinetics. Marcel Dekker, Inc., New York, 1975).

(e) Uptake from subcutaneous (sc), intraperitoneal (ip), and oral (Po) routes, Oral dosing can be performed by gavage with a small stomach tube to DecapiCone-restrained animals. The agent can be administered in a single dose of 50 mg/kg to a series of 12 mice. At specific times following administration (e.g., 15, 30, 60, 90, 150 and 240 minutes), two mice are sacrificed and their plasma samples prepared and analyzed by HPLC as described above in (d). Following decapitation, the site of drug application in each animal's carcass is dissected and inspected visually for evidence of precipitation.

The data are analyzed to obtain an estimate of the rate and extent of uptake (i.e. "area under the curve"). This is particularly important for the oral route, because the bio-availability of prodrug forms will be used to select drug candidates for oral use.

Evaluation of results of (a)–(e). A wide variety of "negative" properties prevent or limit a candidate's progression to further testing. Examples of such negative properties include:

(i) significant acute toxicity at plasma levels required for efficacy;

(ii) insufficient rate of uptake from one of the three non-iv sites;

(iii) an unusually short plasma half life (e.g., <15 minutes); and (iv) any combination of marginal levels of these properties.

Bacterial Infection Models

The mouse thigh infection model has been pioneered and used by Craig and colleagues (Craig, W. A., Redington, J. and S. C. Ebert (1991) J. Antimicr. Chemother. 27:Suppl C, 29–40; Leggett, J. E., Ebert, S., Fantin, B. and W. A. Craig (1991) Scand. J. Inf. Dis. 74:179–184). It represents a rational, flexible, cost-effective, and reproducible experimental approach for predicting the efficacy of a bacterial infection in a human patient. It is particularly useful in the present invention, because it is adaptable to the use of clinically relevant strains of Staphylococcus and Enterococcus.

Mice are made neutropenic to render them susceptible to infection with a wide variety of bacteria. The mice are then infected by careful intramuscular (im) injection of a predetermined number of the test bacteria into the thigh. The infected mice are typically divided into at least 3 groups. One group receives treatment with the test agent, one receives treatment with an agent of known efficacy (positive control, i.e., vancomycin in the case of S. aureus and E. fecalis), and the other (control) group receives only the vehicle used to convey the agents. Just before treatment begins, and at an appropriate time(s) after infection (for example, 24 hours) the animals are sacrificed. The infected thigh of each animal is homogenized in sterile saline, and the bacterial concentration in the homogenate is determined by dilution and plating.

Typically, the infection is designed to avoid death of untreated animals in the period of experimental observation. The inoculum and the period of the experiment are chosen such that the number of bacteria in the thigh of an untreated infected animal increases by no more than 2–3 logs. The efficacy of the test agent, which is compared to that of the positive control, is typically based on the capacity of a given dose to prevent this increase and to reduce the bacterial load to some specific fraction of the load which was present at the beginning of treatment. For example, vancomycin given ip in saline at 40 mg/kg every four hours produces a range of 2–4 log reduction in S. aureus proliferation compared with control thighs in this experiment.

The prodrugs of the invention are tested in this model initially by the ip route and at doses suggested by the results of the ip/ip in vivo test. Compounds displaying significant efficacy (i.e., comparable to that of vancomycin) against S. aureus or any of the bacterial strains used in the thigh model are examined for acute and chronic toxicity in mice.

Testing can be carried out as follows. Six week old pathogen-free ICR/Swiss mice are rendered neutropenic ($<10^2$ per $mm^3$) by ip injection of two doses of cyclophosphamide, 4 days (150 mg/kg) and 1 day (100 mg/kg) before the infection. Thigh infection is produced by intramuscular injection of 0.1 ml of Mueller-Hinton Broth containing approximately $10^6$ colony forming units (CFU) of methicillin-sensitive Staphylococcus aureus (ATCC # 29213). Treatment with the test agent and the positive control agent (vancomycin) is initiated at 2 hours post-infection, using a route (Po, ip, or sc), schedule, and dosing regimen determined by the agent's in vitro potency and specific pharmacokinetic properties.

The compounds are given by ip injection of 0.05 ml of a saline solution. Both vancomycin (as saline solution) and test compounds are given in multiple doses of 40 mg/kg delivered at 2, 6, 12, and 18 hours post-infection. The same schedule will be used for administration of control vehicles. Just before the first treatment, three animals are sacrificed for determination of initial bacterial load. At 24 hours post infection all remaining animals are killed. The infected thighs are removed, homogenized in 10 ml of chilled sterile saline in a POLYTRON® tissue homogenizer, and worked up as described herein. Results are expressed as the log reduction in bacterial growth as a fraction of that in vehicle-treated animals.

EXAMPLES

In order that the invention may be more fully understood, the following specific examples are provided. The examples do not limit the scope or content of the invention in any way.

Example 1

Synthesis of Amino Acid Ester Prodrugs

The prodrug 3-(L-valylbutyl)-EMAU (Val-B-EMAU, 4a) was synthesized as a hydrochloride. The structure was confirmed by NMR. The compound had high solubility in water. At 25° C., Val-B-EMAU had a solubility in water of >10 mg/ml, whereas the ultimate drug HB-EMAU had a solubility of about 0.03 mg/ml. Two different synthesis methods were used.

Method A

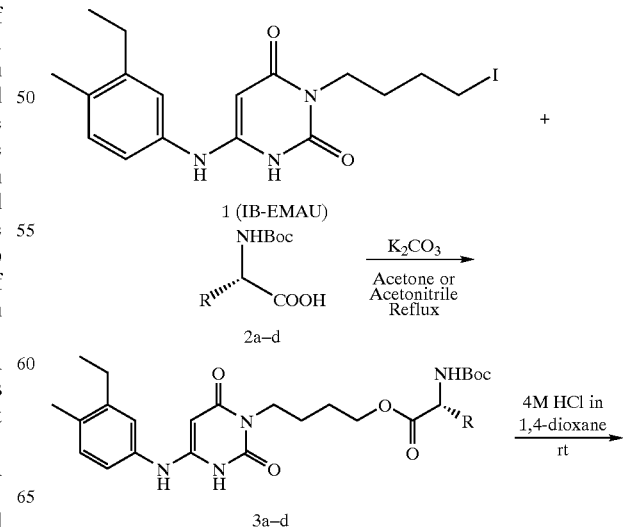

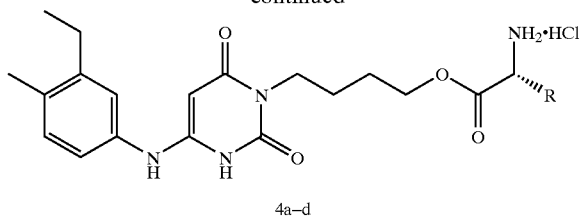

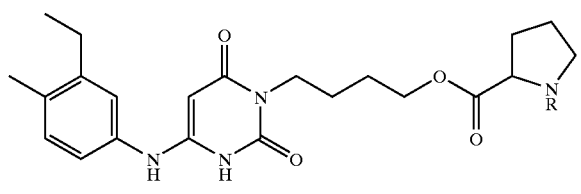

3e •R = Boc
4e •R = H•HCL

R: a. (CH₃)₂CH; b. HOCH₂; c. Me; d. PhCH₂.

Boc-protected α-amino acid esters 3a–d: A stirred mixture of 3-(4-iodobutyl)-6-(3-ethyl-4-methylanilino)uracil 1 (IB-EMAU) (1 eq.), Boc (benzyloxycarbonyl)-protected α-amino acids 2a–d (4 eq.), and anhydrous potassium carbonate (3 eq.) in acetone or acetonitrile was heated to reflux until disappearance of the starting material 1. The reaction mixture was cooled to room temperature, and the solvent was removed. Water was added to the residue to form a mixture, which was extracted with chloroform. The combined organic layers were washed with water and dried over Na₂SO₄. The solvent was evaporated, and the residue was purified by chromatography on silica gel with chloroform-:methanol (99:1 to 99:2) as eluent to give Boc protected α-amino acid esters 3a–d.

3a yield: 72%. ¹H NMR (DMSO-d₆): δ 0.86 (d, 6 H, 2×CH₃), 1.14 (t, 3 H, CH₃CH₂), 1.37 (s, 9 H, 3×CH₃), 1.54 (m, 4 H, 2×CH₂), 1.98 (m, 1 H, CHMe₂), 2.24 (s, 3 H, CH₃Ar), 2.57 (q, 2 H, CH₂CH₃), 3.71 (t, 2 H, CH₂N), 3.80 (m, 1 H CHNHBoc), 4.04 (m, 2 H, CH₂O), 4.72 (s, 1 H, C₅—H), 6.80 (br, 1 H, NHBoc), 7.05 (m, 3 H, Ar—H), 8.13 (s, 1 H, NH), and 10.46 (s, 1 H, NH).

3b yield: 70%. ¹H NMR (DMSO-d₆): δ 1.14 (t, 3 H, CH₃CH₂), 1.38 (s, 9 H, 3×CH₃), 1.54 (m, 4 H, 2×CH₂), 2.24 (s, 3 H, CH₃Ar), 2.57 (q, 2 H, CH₂CH₃), 3.30 (br, 1 H, NHBoc), 3.62 (m, 2 H, CH₂OH), 3.71 (t, 2 H, CH₂N), 4.03 (m, 3 H, CH₂O and CHNHBoc), 4.72 (s, 1 H, C₅—H), 4.86 (t, 1 H, OH), 6.90–7.20 (m, 4 H, NHBoc and Ar—H), 8.11 (s, 1 H, NH), and 10.42 (s, 1 H, NH).

3c yield: 76%. ¹H NMR (DMSO-d₆): δ 1.14 (t, 3 H, CH₃CH₂), 1.20 (d, 3 H, CH₂), 1.38 (s, 9 H, 3×CH₃), 1.54 (m, 4 H, 2×CH₂), 2.24 (s, 3 H, CH₃Ar), 2.57 (q, 2 H, CH₂CH₃), 3.71 (t, 2 H, CH₂N), 3.90–4.10 (m, 3 H, CH₂O and CHNHBoc), 4.72 (s, 1 H, C₅—H), 6.90–7.20 (m, 4 H, NHBoc and Ar—H), 8.11 (s, 1 H, NH), and 10.42 (s, 1 H, NH).

3d yield: 64%. ¹H NMR (DMSO-d₆): δ 1.13 (t, 3 H, CH₃CH₂), 1.32 (s, 9 H, 3×CH₃), 1.48 (m, 4 H, 2×CH₂), 2.24 (s, 3 H, CH₃Ar), 2.57 (q, 2 H, CH₂CH₃), 2.80–3.00 (m, 2 H, CH₂Ph), 3.69 (m, 2 H, CH₂N), 4.00 (m, 2 H, CH₂O), 4.11 (m, 1 H, CHNHBoc), 4.73 (s, 1 H, C₅—H), 6.90–7.35 (m, 9 H, NHBoc and Ar—H), 8.10 (s, 1 H, NH), and 10.43 (s, 1 H, NH).

3e yield: 78%. ¹H NMR (DMSO-d₆): δ 1.17 (t, 3 H, CH₃CH₂), 1.35 (m, 9 H, 3×CH₃), 1.59 (m, 4 H, 2×CH₂), 1.80 (m, 4 H, 2×CH₂), 2.24 (s, 3 H, CH₃Ar), 2.57 (q, 2 H, CH₂CH₃), 3.40 (m, 2 H, CH₂NBoc), 3.71 (m, 2 H, CH₂N), 4.00–4.16 (m, 3 H, CHCO₂CH₂), 4.04 (m, 2 H, CH₂O), 4.72 (s, 1 H, C₅—H), 6.92–7.16 (m, 3 H, Ar—H), 8.11 (s, 1 H, NH), and 10.43 (s, 1 H, NH).

Prodrugs 4a–e. A solution of Boc-protected α-amino acid esters 3a–d in 1,4-dioxane was added to a stirred solution of 4M hydrogen chloride in 1,4-dioxane. The reaction mixture was stirred at room temperature until disappearance of starting materials 3a–d. The solvent was removed under reduced pressure. The salt 4a–e was precipitated with dry diethyl ether, filtered, and dried under vacuum.

4a yield: 84%. ¹H NMR (DMSO-d₆): δ 0.92 (dd, 6 H, 2×CH₃) 1.14 (t, 3 H, CH₃CH₂), 1.58 (m, 4 H, 2×CH₂), 2.16 (m, 1 H, CHMe₂), 2.24 (s, 3 H, CH₃Ar), 2.57 (q, 2 H, CH₂CH₃), 3.72 (t, 2 H, CH₂N), 3.91 (m, 1 H, CHNH₃), 4.20 (m, 2 H, CH₂O), 4.72 (s, 1 H, C₅—H), 7.05 (m, 3 H, Ar—H), 8.36 (s, 3 H, NH₃), 8.52 (s, H, NH) and 10.58 (s, 1 H, NH).

4b yield: 85%. ¹H NMR (DMSO-d₆): δ 1.14 (t, 3 H, CH₃CH₂), 1.59 (m, 4 H, 2×CH₂), 2.24 (s, 3 H, CH₃Ar), 2.57 (q, 2 H, CH₂CH₃), 3.67–4.00 (m, 5 H, CH₂N, CHNH₃, and CH₂OH,), 4.10–4.20 (m, 2 H, OH and CH₂O), 4.74 (s, 1 H, C₅—H), 7.05 (m, 3 H Ar—H), 8.39 (s, 3 H, NH₃), 8.58 (s, H, NH) and 10.62 (s, 1 H, NH).

4c yield: 82%. ¹H NMR (DMSO-d₆): δ 1.14 (t, 3 H, CH₃CH₂), 1.40 (d, 3 H, CH₃), 1.60 (m, 4 H, 2×CH₂), 2.24 (s, 3 H, CH₃Ar), 2.57 (q, 2 H, CH₂CH₃), 3.75 (t, 2 H, CH₂N), 4.10–4.18 (m, 3 H, CHNH₃ and CO₂CH₂), 4.74 (s, 1 H, C₅—H), 7.05 (m, 3 H, Ar—H), 8.37 (s, 3 H, NH₃), 8.60 (s, H, NH), and 10.62 (s, 1 H, NH).

Method B

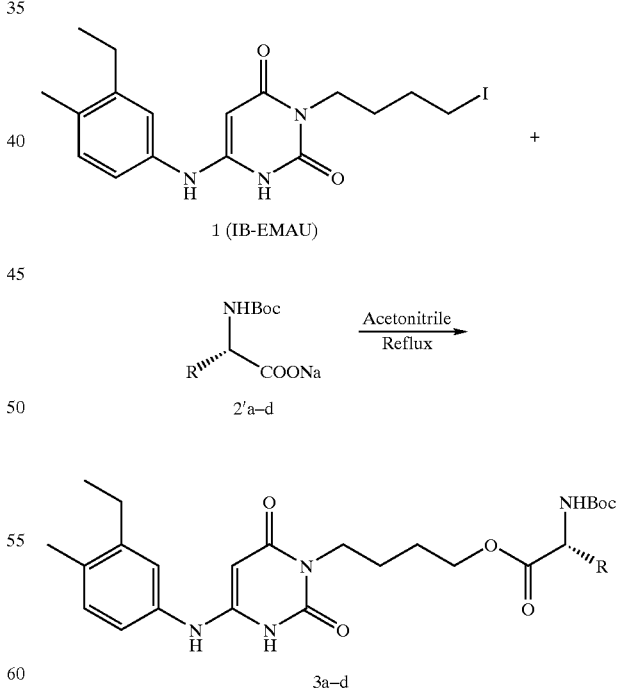

Alternate methodfor Boc-protected α-amino acid esters 3a–d. A stirred mixture of 3-(4-iodobutyl)-6-(3-ethyl-4-methylanilino)uracil 1 (1 eq.), Boc protected α-amino acid, sodium salt 2'a–d (4 eq.) in acetonitrile was heated to reflux until disappearance of the starting material 1. The reaction mixture was cooled to room temperature, and the solvent was removed. Water was added to the residue to form a mixture, which was extracted with chloroform. The combined organic layers were washed with water and dried over $Na_2SO_4$. The solvent was evaporated, and the residue was purified by chromatography on silica gel with chloroform:methanol (99:1 to 99:2) as eluent to give Boc-protected oc-amino acid esters 3a–d.

Example 2

Biological Activity, In Vitro Decomposition, and In Vivo Conversion of 3-(L-valylbutyl)-EMAU Val-B-EMAU (produced in Example 1) was found to be a potent inhibitor of DNA pol III and had antibacterial activity comparable to that of the drug HB-EMAU, as shown in Table 1.

TABLE 1

Activity of HB-EMAU and Val-B-EMAU

|  | $K_i$ ($\mu M$) | MIC ($\mu g/ml$) | | |
|---|---|---|---|---|
| Compound | B. subtilis pol III | B. subtilis | S. aureus | E. fecalis |
| Val-B-EMAU (4a) | 0.53 | <3.1 | 11 | 6 |
| HB-EMAU | 0.19 | <3.1 | 6 | 6 | appearance of HB-EMAU. The rate of formation of the drug and the rate of decay of the prodrug had doubling and half-life times, respectively, of about 30 minutes. In contrast, the estimated half-life of Val-B-EMAU in physiological saline at 37° C. was greater then 5000 hours. The mechanism for the decomposition of Val-B-EMAU by plasma is presumed to involve esterases in the circulation.

Solutions of Val-B-EMAU in saline were next injected into the tail veins of mice at a dose of 25 mg/kg body weight. Animals were sacrificed at various times after dosing, and plasma was isolated and subjected to HPLC analysis. As illustrated in FIG. 1, the initial high concentration of Val-B-EMAU fell with a simultaneous increase in HB-EMAU concentration. The half life of Val-B-EMAU in plasma was 34 minutes, nearly identical to that found in vitro. HB-EMAU concentration peaked at about 20 minutes, and the half life was about 43 minutes.

To further investigate the antibacterial and/or DNA pol III inhibitory activity of various drug compounds, various ester-containing moieties N-linked to the EMAU core were produced as described in Example 1. These prodrugs were assayed for inhibition of B. subtilis DNA pol III and antibiotic activity against a number of bacteria. The results are summarized in Table 2.

TABLE 2

Prodrugs having the EMAU core

| N3-subsituted moiety | $Ki(\mu M)$ | MIC($\mu$/ml) | | | | | | | |
|---|---|---|---|---|---|---|---|---|---|
|  | B. subtilis DNA Pol III | B. subtilis | S. aureus | MRSA | MRSA2 | E. fecalis | E. fecium | VRE | E. coli |
| $(CH_2)_4$-OCOCH(iPr)NH-Boc | 4.9 | 2.5 | >20 | >20 | >20 | >20 | >20 | >20 | >20 |
| $(CH_2)_4$-OCOCH($CH_2OH$)NH-Boc | 1.5 | 5 | 20 | 20 | 20 | 5 | 10 | 5 | >20 |
| $(CH_2)_4$-OCOCH($CH_2$)$_3$NH-Boc | 3.2 | <1.25 | 10 | 20 | 10 | 10 | 10 | 10 | >20 |
| $(CH_2)_4$-OCOCHCH$_3$NH$_3^+$Cl$^-$ | 0.18 | 2.5 | 20 | 20 | 20 | 10 | 10 | 10 | >20 |
| $(CH_2)_4$-OCOCH(iPr)NH$_3^+$Cl$^-$ | 0.53 | 4 | 17 | 33 | 33 | 17 | 33 | 8 | >33 |
| $(CH_2)_4$-OCOCH($CH_2OH$)NH$_3^+$Cl$^-$ | 0.01 | 10 | >20 | >20 | >20 | 20 | 20 | 20 | >20 |
| $(CH_2)_4$-OCOCH($CH_2Ph$)NH$_3^+$Cl$^-$ | 6.2 | >20 | >20 | >20 | >20 | >20 | >20 | >20 | >20 |

Abbreviations:
Competitive Inhibitor Constant (Ki), Minimal Inhibitory Concentration (MIC), methicillin-resistant S. aureus strains (MRSA and MRSA2), and vancomycin-resistant E. fecium (VRE).

Both HB-EMAU and Val-B-EMAU were effective antibiotics against B. subtilis, S. aureus, and E. fecalis, as shown by the low MIC values (below 20 $\mu g/ml$) and the low Ki values (below 1 $\mu M$). The lower the Ki or MIC, the higher the inhibitory or antibiotic activity. The activity of the prodrug may reflect direct action of the compound or may be a result of the prodrug's hydrolysis to HB-EMAU in cell culture medium. The anti-pol III and/or antibacterial activities of the prodrug are advantages but are not essential; it is the conversion of prodrug to the ultimate drug that is of importance.

Incubation of Val-B-EMAU in mouse plasma at 37° C., followed by HPLC analysis of the compound in the plasma indicated that the prodrug disappeared coincident with the The data of Table 2 indicates that, while some prodrugs containing certain N3-substituted moieties (e.g., $(CH_2)_4$-OCOCH($CH_2Ph$) NH$_3^+$cl$^-$) were relatively ineffective antibiotics against all bacteria tested, as shown by a MIC value of greater than 20 $\mu g/ml$, prodrugs having other N3-substituted moieties (e.g., $(CH_2)_4$-OCOCH($CH_2$)$_3$NH-Boc) exhibited strong antibiotic activity against some bacteria, as shown by a MIC value of less than 15 $\mu g/ml$.

Figure 2:
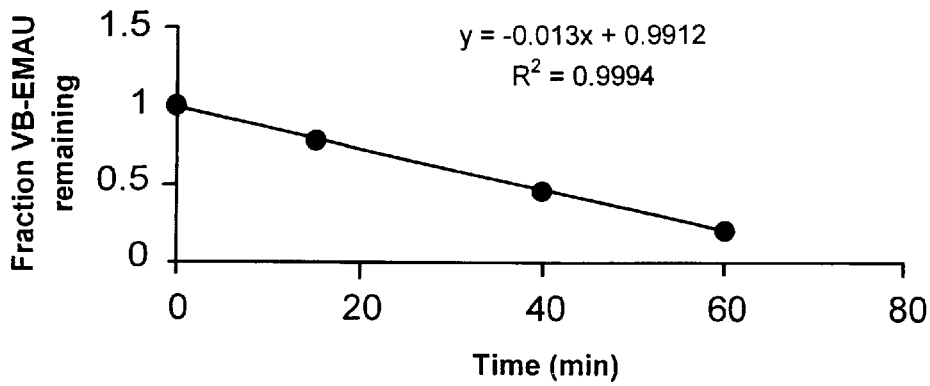
FIG. 2 is a line graph of time versus fraction of prodrug remaining.

To further define the conversion rate of Val-B-EMAU (4a), the prodrug was incubated in 80% mouse plasma. At 37° C., the prodrug was converted to the corresponding HB-EMAU drug with a prodrug half-life of 37.8 minutes (FIG. 2), while the prodrug in physiological saline exhibited a half-life of 450 to 500 hours.

Figure 3:
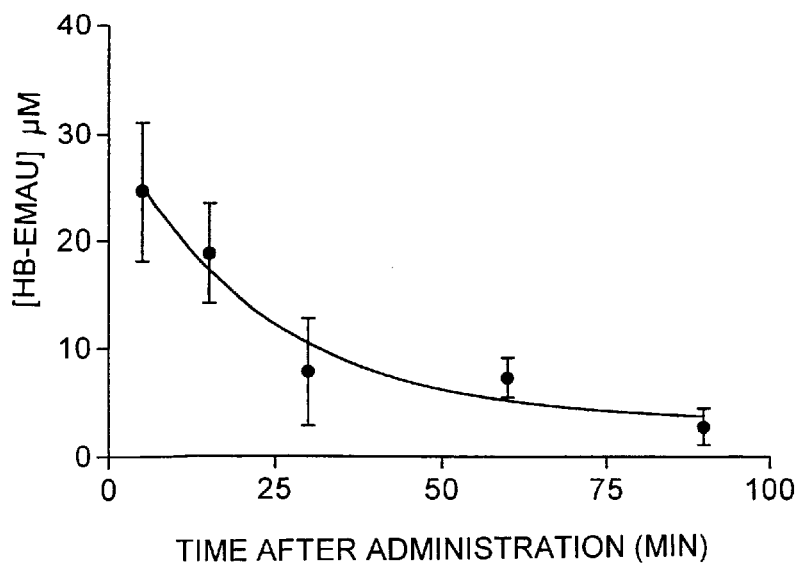
FIG. 3 is a line graph of time after administration versus drug concentration.

Upon intravenous administration to mice at a dose of 25 mg/Kg body weight, Val-B-EMAU (4a) was rapidly converted to HB-EMAU which was, in turn, eliminated with a half-life of 15.6 minutes (FIG. 3). Each value plotted in FIG. 3 represents the average of four measurements, each in a different animal.

Figure 4:
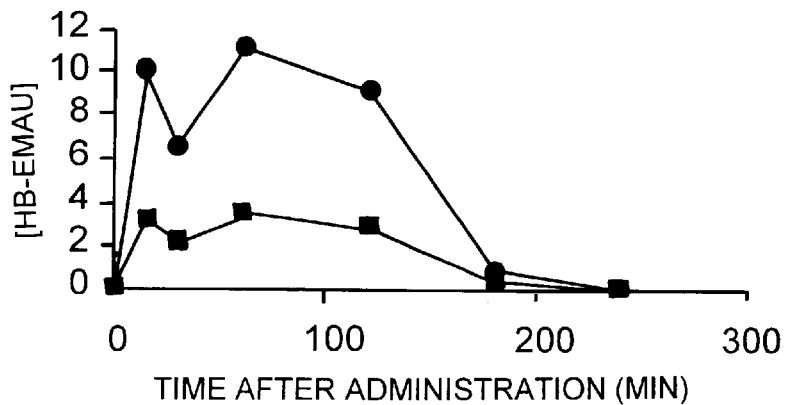
FIG. 4 is a line graph of time after administration versus drug concentration. The solid circles represent drug concentration in $\mu M$, and the solid squares represent drug concentration in $\mu g/ml$.

Following oral administration of Val-B-EMAU (4a) in physiological saline to mice at a dose of 100 mg/Kg body weight, the plasma level of HB-EMAU peaked at 60 minutes, then fell slowly with no detectable HB-EMAU at four hours after administration. FIG. 4 summarizes the results of this experiment. Each value plotted in FIG. 4 is an average of two measurement, each in a different animal. The peak concentration of HB-EMAU following administration of VB-EMAU was 11.2 $\mu$M (3.5 $\mu$g/ml) with an area under the curve of 447 $\mu$g/ml per minute, which corresponds to an oral bioavailability of 2.5%. Because the area under the curve for HB-EMAU was estimated as 0.1%, a 25-fold increase over direct intravenous administration was attained.

Example 3

Synthesis of N3-Substituted EMAU Compounds 3-(2-Hydroxyethyl) and 3-(3-hydroxypropyl) derivatives of EMAU were prepared as described below. Methoxyalkylureas were prepared in high yields by standard methods (Vogel, A. Textbook of Practical Organic Chemistry. 4th ed. Longman: Harlow, 1978, pp.732–735). Reaction of the ureas with diethyl malonate in the presence of sodium ethoxide gave N-(methoxyalkyl)barbituric acids. Selective 6-chlorination of the intermediate barbituric acids was done by modification of a standard method (Nubel, G. and W. Pfleiderer (1962) Chem. Ber. 95:1605–1614) using low temperatures and benzyltriethylammonium chloride as a catalyst (Lee, N., Y.-W. Kim, K.H. Kim and D.-K. Kim (1997) J. Heterocycl. Chem. 34:659). Fusion of the 6-chlorouracils with 3-ethyl-4-methylaniline gave the methoxyalkyl compounds ME-EMAU and MP-EMAU, in high yields. 3-Ethyl-4-methylaniline was prepared as described in the literature (Thomsen, A. D. and H. Lund (1969) Acta Chem. Scand. 23:2931–2932; Minlon, H. (1949) J. Chem. Soc. 3301–3303.) Briefly, p-acetamidotoluene was acetylated under Friedel-Crafts conditions (CH$_3$COCl,AlCl$_3$), and the resulting acetophenone was reduced under Wolff-Kishner conditions (NH$_2$NH$_2$ ethylene glycol) to give 3-ethyl-4-methylacetanilide. Basic hydrolysis gave 3-ethyl-4-methylaniline.

The compounds were demethylated by treatment with trimethylsilyl iodide in chloroform (Heathcock, C. H. and R. Ratcliffe (1971) J. Am. Chem. Soc. 93:1746–1757) under carefully controlled conditions to afford the desired hydroxyalkyl derivatives HE-EMAU and HP-EMAU. Conditions of demethylation and isolation were critical, because both products can undergo cyclization to the cyclic ethers, especially the hydroxypropyl derivative.

The higher homologs HB-EMAU and HPn-EMAU, i.e., the 4-hydroxybutyl and 4-hydroxypentyl derivatives, can be made in the same manner, and are more stable chemically.

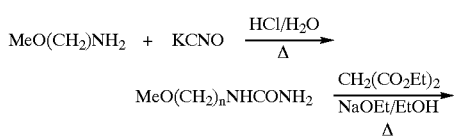

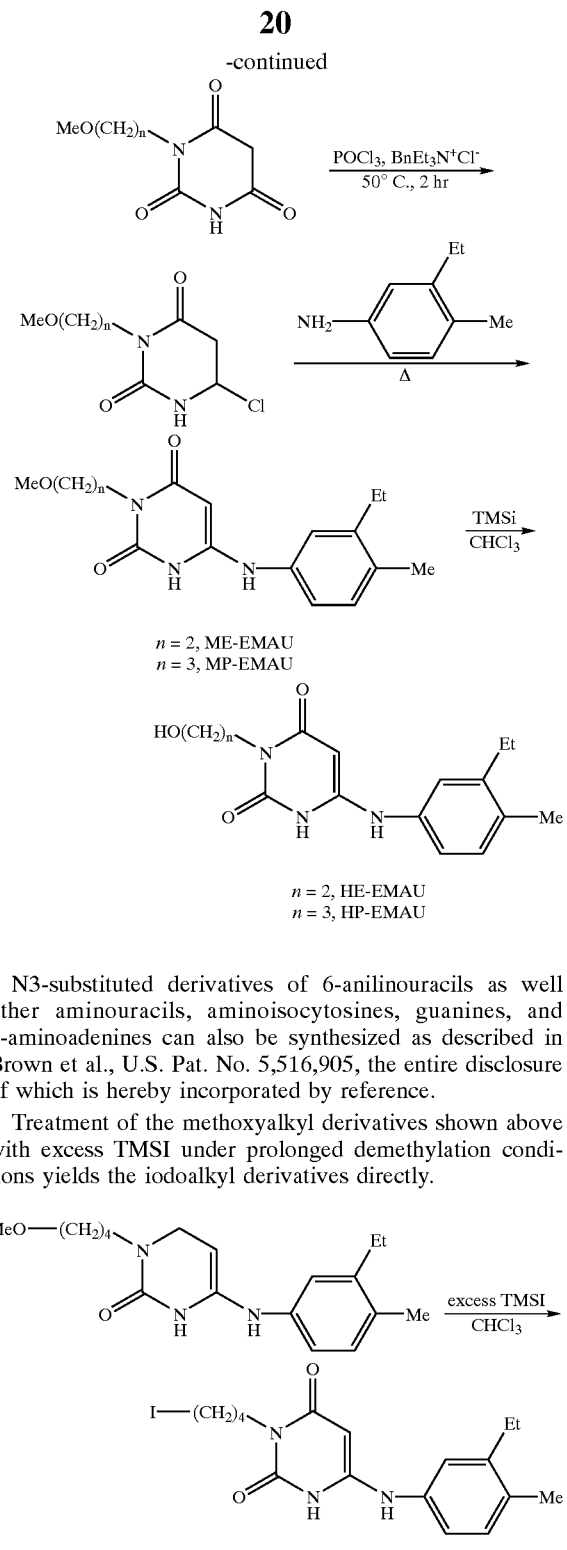

N3-substituted derivatives of 6-anilinouracils as well other aminouracils, aminoisocytosines, guanines, and 2-aminoadenines can also be synthesized as described in Brown et al., U.S. Pat. No. 5,516,905, the entire disclosure of which is hereby incorporated by reference.

Treatment of the methoxyalkyl derivatives shown above with excess TMSI under prolonged demethylation conditions yields the iodoalkyl derivatives directly.

These iodoalkyl derivatives can be used as intermediates in the prodrug synthesis as described in Examples 6 and 10.

Example 4

Small Scale Synthesis

6-Anilinouracils were synthesized using small scale synthetic methods. One milligram quantities of 3-(3-methoxypropyl)-6-chlorouracil were heated with 42 substituted anilines in micro-test tubes at 130° C. for 20 minutes. The reaction mixtures were dissolved in DMSO and assayed directly for antibacterial activity. The activities of these compounds are summarized in Table 3.

TABLE 3

Antibacterial activity of crude compounds made by small scale synthesis

| Anilines | MIC (μg/mL), B. subtilis | Anilines | MIC (μg/mL), B. subtilis |
|---|---|---|---|
| — | >100 | 3-Cl | >100 |
| 3-Me | 100 | 4-Cl | 100 |
| 4-Me | 50 | 3,4-diCl | 6.25 |
| 3,4-diMe | 6.26 | 3,5-diCl | >100 |
| 3,5-diMe | 50 | 3-Br | >100 |
| 3-Et | 6.25 | 3,4-diBr | 3.13 |
| 4-Et | 50 | 3-I | 25 |
| 3-Et-4-Me[MP-EMAU] | 3.13 | 4-I | 100 |
| 4-Pr | >100 | 3-F | >100 |
| 4-iPR | >100 | 4-F | >100 |
| 4-iBU | >100 | 3,4-diF | >100 |
| 3-CH₂OH | >100 | 3,4,5-triF | >100 |
| 3-CH₂OH-4-Me | >100 | 3-Cl-4-F | 50 |
| 3-CH(OH)CH₃ | >100 | 3-Cl-4-OMe | 50 |
| 3-OMe | >100 | 3-Cl-4-Me | 3.13 |
| 3,4-diOMe | >100 | 3-CF₃-4-Cl | >100 |
| 3-CN | >100 | 3-MeA-Br | 6.25 |
| 4-CN | >100 | 3-CF3-4-Br | >100 |
| 3-NO₂ | >100 | 3-I-4-Me [MP-IMAU] | 1.57 |
| 4-OH | >100 | 3,5-diOCF₃ | >100 |

As shown in Table 3, some of the crude prodrugs made using small scale synthetic methods exhibited significant antibacterial activity against *B. subtilis* (e.g., those having a MIC value of <20 μg/ml), while others did not exhibit any measurable antibiotic activity (e.g., those having a MIC value of >100 μg/ml). The relative activities paralleled the inhibitory activities of the corresponding 3-H compounds against *B. subtilis* DNA pol III (Wright, G. E. and N. C. Brown (1980), J. Med. Chem. 23:24–28; and Wright, G. E. and J. Gambino (1984), J. Med. Chem. 27:181–185).

Example 5

Biolopical Properties of Selected N3-Substituted EMAU Derivatives

The competitive inhibitor constants (Ki) of selected EMAU compounds were determined with three different pol IIIs: the pol III enzyme from *Bacillus subtilis* (BS pol III), and the pol III enzymes of the clinically relevant pathogens, *Enterococcus fecalis* (EF pol III) and *Staphylococcus aureus* (SA pol 111). The results are summarized in Table 4.

TABLE 4

Inhibition of pol III by hydrophilic EMAU derivatives

| | | $K_I$ (μM) | | |
|---|---|---|---|---|
| Compound | N3 Substituent | Bs pol III | SA pol III | EF pol III |
| HE-EMAU | —CH₂CH₂OH | 0.20 | 0.98 | 0.17 |
| ME-EMAU | —CH₂CH₂OCH₃ | 0.19 | 0.82 | 0.16 |
| HP-EMAU | —CH₂CH₂CH₂OH | 0.33 | 0.42 | 0.14 |
| MP-EMAU | —CH₂CH₂CH₂OCH₃ | 0.24 | 0.82 | 0.19 |
| EMAU | —H | 0.25 | 0.81 | 0.26 |

The Ki values listed in Table 4 is the average of 3 determinations, with a standard deviation of 13.4%. The results in Table 4 indicate that the four compounds are effective pot III inhibitors (Ki less than 1 μM), sharing approximately the same potency for a given enzyme. With respect to both absolute potency and relative activity against the three pol III enzymes, each compound behaved like the unsubstituted EMAU.

The minimal inhibitory concentrations (MICs) of the four N3-substituted agents and EMAU were determined for *B. subtilis* (BS), methicillin-sensitive and resistant *S. aureus* (SA & MRSA), vancomycin-sensitive and resistant *E. fecalis* (EF& VREF), vancomycin-resistant *E. fecium* (VREF*), and *E. coli* (EC) as a Gram-negative control. The data are summarized in Table 5.

TABLE 5

Antibacterial activity of hydrophilic EMAU derivatives

| | MIC (μg/mL) | | | | | | | |
|---|---|---|---|---|---|---|---|---|
| Compound | BS | SA | MRSA1 | MRSA2 | EF | VREF | VREF* | EC |
| HE-EMAU | 1.1 | 8.7 | 17.4 | 17.4 | 6.5 | 8.7 | 8.7 | >>35 |
| ME-EMAU | 1.0 | 10.3 | 8.3 | 12.4 | 6.2 | 6.2 | 8.3 | >>35 |
| HP-EMAU | 1.0 | 4.1 | 8.3 | 8.3 | 4.1 | 4.1 | 4.1 | >>35 |
| MP-EMAU | 0.5 | 3.9 | 3.9 | 3.9 | 1.9 | 1.9 | 3.9 | >>35 |
| EMAU | 12 | 25 | 25 | 25 | 25 | 25 | 25 | >>35 |

The N3-substituted agents were significantly more potent (e.g., having a MIC value of <10 μg/ml) than EMAU as inhibitors of bacterial growth. Among the four, the methoxypropyl and hydroxypropyl derivatives were the most potent and the broadest with respect to "spectrum," displaying strong activity against all three Gram-positive genera, including those resistant to conventional antibiotics. As expected, the four compounds were Gram-positive-specific. None of them displayed discernible activity against the Gram-negative *E. coli* control (MIC >>35).

The efficacy of the propyl derivatives was tested against murine staphylococcal infection in vivo. A simple "ip/ip" system was used, in which 20 gram mice (10 each) were injected ip (intraperitoneally) with a lethal dose ($2.3 \times 10^7$ CFU) of the methicillin-sensitive Smith strain of *S. aureus*. The mice were then immediately injected ip with the antibiotic agent as a 1:9 mixture of DMSO:peanut oil. Vancomycin was used as the positive control drug. At 10 mg/kg, HP-EMAU protected all mice, as did vancomycin at 20 mg/kg. Even at half that dose (5 mg/kg), HP-EMAU protected 70% of the animals. MP-EMAU was weaker than the hydroxy derivative, protecting roughly 50% of animals at the higher (10 mg/kg) dose and none at the lower dose.

Example 6

Synthesis of HB-EMAU and MB-EMAU

The 3-(4-methoxybutyl) and 3-(4-hydroxybutyl) derivatives of EMAU (MB-EMAU and HB-EMAU, respectively), were prepared by the same route as that described for the ethyl and propyl analogs, as shown below. During demethylation, no evidence of cyclization of the HB compound was observed.

Another product was obtained. This product was identified as the 4-iodobutyl derivative, IB-EMAU, by mass spectrometry. The relative yield of this side product increased during prolonged treatment with trimethylsilyl iodide (TMSI). The iodobutyl compound exhibited significant anti-pol III and antibacterial activities. This compound can be used to prepare amino acid ester prodrugs, as described above.

Example 7

Biological Activit of HB-EMAU and HB-IMAU

The hydroxybutyl and iodobutyl derivatives of EMAU and IMAU were potent inhibitors of pol III and Gram-positive bacterial growth (MIC value <15 μg/ml; Ki <1 μM), as shown in Table 6.

tinued for 24 hours. The results were similar to those reported for the ethyl and propyl compounds, and were nearly identical for both HB-EMAU and HB-IMAU at all three concentrations.

Both hydroxybutyl compounds were tested at 10 mg/kg in the mouse protection experiment against lethal *S. aureus* infection described in Example 4 above. Both compounds protected mice from death during the four day experiment. HB-EMAU protected all ten animals. HB-IMAU protected nine of ten animals. The vancomycin control drug at 20 mg/g protected all ten mice.

Example 8

Preparation of Halomethylanilinouracil Compounds

The 6-(3-hydroxymethyl-4-methylanilino) compound is prepared by demethylation of the methoxybutyl derivative, followed by conversion to the meta(halomethyl) derivative, as illustrated below. The benzylic hydroxyl group is expected to be displaced by hydrohalic acids in preference to the primary hydroxyl of the hydroxybutyl side chain.

TABLE 6

Activity of EMAU and IMAU derivatives

| Compound | N3-Substituent (X) | Moiety on Aromatic Ring (Y) | $K_i(\mu M)$* | MIC(μg/mL) | | |
| --- | --- | --- | --- | --- | --- | --- |
| | | | | B. subtilis | S. aureas | E. fecalis |
| HB-EMAU | $C_4H_8OH$ | Et | 0.18 | <3.1 | 6 | 6 |
| MB-EMAU | $C_4H_8OMe$ | Et | 0.43 | <3.1 | 6 | 6 |
| IB-EMAU | $C_4H_8I$ | Et | 0.36 | <3.1 | 12 | 6 |
| HB-IMAU | $C_4H_8OH$ | I | 0.22 | <3.1 | 6 | 6 |
| ME-IMAU | $C_4H_8OMe$ | I | 0.54 | <3.1 | 6 | 3 |
| IB-IMAU | $C_4H_8I$ | I | 0.66 | <3.1 | 6 | 6 |

*Inhibition constant vs. *B. subtilis* DNA pol III

The IMAU compound was identified from the small scale synthesis procedure of Example 4. The N3-substituted substituent (X) and the moiety on the aromatic ring (Y) correspond to the following compound.

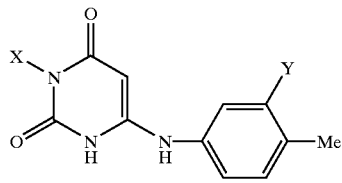

Both HB-EMAU and HB-IMAU were bactericidal for *S. aureus* at concentrations of 2, 4, and 8× their MIC values. Killing was evident within 3 hours of incubation and con-

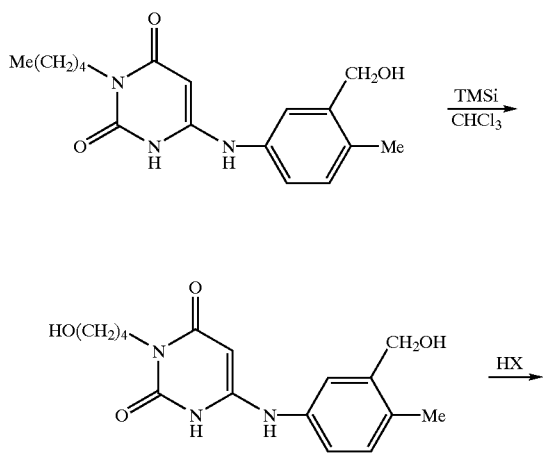

-continued

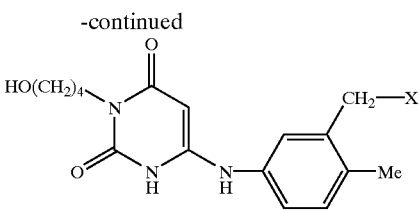

X = Cl, Br, I

Example 9

Preparation of HB-6-benzylaminouracils

These compounds can be prepared using the synthetic procedures described above. 3-(4-Methoxybutyl)-6-chlorouracil and substituted benzylamines are used as the starting materials.

Example 10

Production of Aminoisocytosine Guanine and Aminoadenine Prodrugs

Prodrugs of the aminoisocytosine, guanine, or aminoadenine derivatives are prepared by following synthetic methods analogous to the procedures described in Example 1 or Method A or B, using the corresponding N-iodoalkyl substituted derivative of aminoisocytosine, guanine, or aminoadenine. The N-iodoalkyl substituted derivatives of the aminoisocytosine, guanine, or aminoadenine compounds are prepared by methods analogous to those described for the aminouracil compounds in Example 3.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All documents cited above are hereby incorporated by reference in their entirety.

What is claimed is:

1. A compound having the formula:

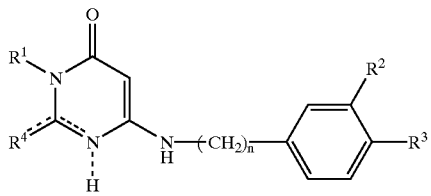

wherein $R^1$ is —$(CH_2)_a$—$(CHOH)_b$—$(CH_2)_c$—O—C(=O)—$(CH_2)_d$—$CHR^5$—$R^6$, wherein a is 1–4; b is 0 or 1; c is 1–5; d is 0–4; n is 0 or 1; $R^5$ is the side chain of a —COOH, —COO$^-$M$^+$, or —NH$_2$; each of $R^2$ and $R^3$ is, independently, linear $C_{1-6}$ alkyl, branched $C_{3-6}$ alkyl, linear $C_{1-6}$ haloalkyl, branched $C_{3-6}$ haloalkyl, halo, or $R^2$ and $R^3$ together are a bivalent moiety having the formula —$(CH_2)_3$—; M$^+$ is a pharmaceutically acceptable counter-ion; and $R^4$ is =O or —NH$_2$, or a pharmaceutically acceptable salt thereof.

2. The compound of claim 1, wherein $R^5$ is the side chain of a naturally-occurring amino acid.

3. The compound of claim 2, wherein the naturally-occurring amino acid is of an animal, a plant, a fungus, or a bacterium.

4. The compound of claim 1, wherein a is 1.

5. The compound of claim 1, wherein b is 0.

6. The compound of claim 1, wherein c is 3.

7. The compound of claim 1, wherein d is 0.

8. The compound of claim 1, wherein d is 1–4.

9. The compound of claim 1, wherein n is 0.

10. The compound of claim 1, wherein $R^2$ is ethyl and $R^3$ is methyl.

11. The compound of claim 1, wherein $R^2$ is iodo and $R^3$ is methyl.

12. The compound of claim 1, wherein $R^5$ is the side chain of an amino acid selected from the group consisting of glycine, alanine, valine, leucine, isoleucine, serine, glutamic acid, glutamine, aspartic acid, asparagine, lysine, phenylalanine, proline, ornithine, beta-alanine, and gamma-aminobutyric acid.

13. The compound of claim 1, wherein the stereochemical configuration of one or more chiral carbons in the compound is S.

14. The compound of claim 13, wherein the one or more chiral carbons is in $R^5$.

15. The compound of claim 1, wherein the stereochemical configuration of one or more chiral carbons in the compound is R.

16. The compound of claim 15, wherein the one or more chiral carbons is in $R^5$.

17. The compound of claim 1, wherein le is —COOH.

18. The compound of claim 1, wherein R $^6$is —NH$_2$.

19. The compound of claim 1, wherein le is —COO$^-$M$^+$.

20. The compound of claim 19, wherein M$^+$ is Na$^+$.

21. The compound of claim 20, wherein the compound is a hydrochloride salt.

22. A composition comprising the compound of claim 1 and a pharmaceutically acceptable carrier.

23. A composition comprising (1) a racemic mixture of the compound of claim 1 and (2) a pharmaceutically acceptable carrier.

24. A composition comprising the compound of claim 14 and a pharmaceutically acceptable carrier.

25. A composition comprising the compound of claim 16 and a pharmaceutically acceptable carrier.

26. A method of treating a Gram-positive bacterial infection in a subject, the method comprising identifying a subject in which treatment of a Gram-positive bacterial infection is desirable; and administering to the subject a therapeutically effective amount of the compound of claim 1.

27. The method of claim 26, wherein the subject is a mammal.

28. The method of claim 27, wherein the mammal is a human.

* * * * *